(12) United States Patent
Oliphant et al.

(10) Patent No.: US 9,051,602 B2
(45) Date of Patent: Jun. 9, 2015

(54) METHODS AND GENOTYPING PANELS FOR DETECTING ALLELES, GENOMES, AND TRANSCRIPTOMES

(75) Inventors: Arnold R. Oliphant, San Diego, CA (US); Kurt A. Krummel, San Diego, CA (US); Haichuan Zhang, San Diego, CA (US); Andrew S. Katz, La Jolla, CA (US)

(73) Assignee: Celula, Inc., San Diego, CA (US)

( * ) Notice: Subject to any disclaimer, the term of this patent is extended or adjusted under 35 U.S.C. 154(b) by 10 days.

(21) Appl. No.: 12/645,129

(22) Filed: Dec. 22, 2009
(Under 37 CFR 1.47)

(65) Prior Publication Data
US 2011/0086769 A1    Apr. 14, 2011

Related U.S. Application Data

(60) Provisional application No. 61/140,063, filed on Dec. 22, 2008, provisional application No. 61/166,188, filed on Apr. 2, 2009, provisional application No. 61/231,232, filed on Aug. 4, 2009.

(51) Int. Cl.
*C12Q 1/68* (2006.01)

(52) U.S. Cl.
CPC ............ *C12Q 1/6806* (2013.01); *C12Q 1/6881* (2013.01)

(58) Field of Classification Search
None
See application file for complete search history.

(56) References Cited

U.S. PATENT DOCUMENTS

| 8,168,389 B2 | 5/2012 | Shoemaker et al. | |
| 2008/0220422 A1* | 9/2008 | Shoemaker et al. | 435/6 |
| 2008/0299562 A1* | 12/2008 | Oeth et al. | 435/6 |

FOREIGN PATENT DOCUMENTS

| WO | WO 2005/022147 A1 | 3/2005 |
| WO | WO 2005/023091 A2 | 3/2005 |
| WO | WO 2007/147079 A2 | 12/2007 |
| WO | WO 2008/098142 A2 | 8/2008 |

OTHER PUBLICATIONS

Hellani et al. (2004) Molecular Human Reproduction vol. 10 No. 11 pp. 847-852.*
Mere et al. (1999) DDT vol. 4 No. 8 pp. 363-369.*
Bianchi (1998) Current knowledge about fetal blood cells in a maternal circulation. J Perinat Med; 26(3):175-185.
Bianchi, D.W. (1999) Fetal cells in the maternal circulation: feasibility for prenatal diagnosis. British Journal of Haematology; 105:574-583.
Chen et al. (2004) Prenatal diagnosis of mosaic distal 5p deletion and review of the literature. Prenatal Diagnosis; 24(1):50-57.
Chiu et al. (2001) Effects of blood-processing protocols on fetal and total DNA quantification in maternal plasma. Clinical Chemistry; 47(9):1607-1613.
Di Naro et al. (2000) Prenatal diagnosis of β-thalassaemia using fetal erythroblasts enriched from maternal blood by a novel gradient. Molecular Human Reproduction; 6(9):571-574.
Eddleman et al (2006) Pregnancy loss rates after midtrimester amniocentesis. Obstetrics & Gynecology; 108(5):1067-1072.
Fisk (1998) Maternal-fetal medicine and prenatal diagnosis. Current Opinion in Obstetrics and Gynaecology; 10(2):81-83.
Huang et al. (2008) A microfluidics approach for the isolation of nucleated red blood cells (NRBCs) from the peripheral blood of pregnant women. Prenatal Diagnosis; 28:892-899.
Sekizawa et al. (1998) Analysis of HLA-DQ α sequences for prenatal diagnosis in single fetal cells from maternal blood. Hum Genet; 102:393-396.
Takabayashi et al. (1995) Development of non-invasive fetal DNA diagnosis from maternal blood. Prenatal Diagnosis; 15:74-77.
Watanabe et al. (1998) Prenatal diagnosis of ornithine transcarbamylase deficiency by using a single nucleated erythrocyte from maternal blood. Hum Genet; 102:611-615.

* cited by examiner

*Primary Examiner* — Suchira Pande
(74) *Attorney, Agent, or Firm* — Knobbe, Martens, Olson and Bear, LLP

(57) ABSTRACT

Disclosed are methods and genotyping panels for detecting alleles, genomes, and transcriptomes in admixtures of two individuals.

11 Claims, No Drawings

METHODS AND GENOTYPING PANELS FOR DETECTING ALLELES, GENOMES, AND TRANSCRIPTOMES

RELATED APPLICATIONS

This application claims priority to the U.S. Provisional Patent Application Ser. No. 61/140,063, filed on Dec. 22, 2008, U.S. Provisional Patent Application Ser. No. 61/166,188, filed on Apr. 2, 2009, and U.S. Provisional Patent Application Ser. No. 61/231,232, filed on Aug. 4, 2009, which are hereby incorporated by reference herein in their entirety.

BACKGROUND OF THE INVENTION

1. Field of the Invention

The present invention is in the field of methods and genotyping panels for detecting alleles, genomes, and transcriptomes in admixtures of two individuals.

2. Description of the Related Art

Prenatal diagnostic methods are primarily aimed at obtaining genetic information of a fetus or an embryo. Prenatal genetic diagnostic methods used in clinical practice essentially involve invasive techniques such as amniocentesis, the removal of chorionic villi, and the removal of fetal blood or tissue biopsies. Those techniques involve obtaining samples directly from the fetus or indirectly from female reproductive structures. Because of the highly invasive nature of those methods, they are prone to complications for the mother or the fetus. Examples of such complications which can be cited in the case of amniocentesis are the risk of infection, feto-maternal hemorrhage with possible allo-immunization, loss of amniotic fluid and abdominal pain. Different studies have estimated the risk of a miscarriage after amniocentesis at 0.06% to 2.1% higher than that of the control group (Eddleman, *Obstet Gynecol* 2006 108(5): 1067-1072). As a result, amniocentesis is only suggested for women for whom the risk of having a child with a clinically significant genetic variation exceeds that of iatrogenic miscarriage, and many physicians prefer to cite a risk commensurate with their experience (typically 1 in 300 to 1 in 500).

In order to limit the use of invasive prenatal diagnostic techniques risking the complications mentioned above and which are generally disagreeable and/or the source of stress for the mother, the development of non-invasive methods constitutes a major aim 1n modern obstetrics.

In particular, fetal cells circulating in maternal blood constitute a source of genetic material that is of potential use for prenatal genetic diagnosis (Bianchi, *Br J Haematol* 1999 105: 574-583; Fisk, *Curr Opin Obstet Gynecol* 1998 10: 81-83). During pregnancy, different cell types of fetal origin traverse the placenta and circulate in the maternal blood (Bianchi, *Br J Haematol* 1999 105: 574-583). Such cell types include lymphoid and erythroid cells, myeloid precursors and trophoblastic epithelial cells (cytotrophoblasts and syncytiotrophoblasts).

Methods for analyzing the genome of fetal cells circulating in maternal blood with a view to prenatal diagnosis have been described, but they remain relatively limited regarding sensitivity and the specificity of the diagnosis (Di Naro et al., *Mol Hum Reprod* 2000 6: 571-574; Watanabe et al., *Hum Genet* 1998 102: 611-615; Takabayashi et al., *Prenat Diagn* 1995 15: 74-77; Sekizawa et al., *Hum Genet* 1998 102: 393-396). The advantage in developing a non-invasive, highly specific prenatal diagnosis method results from the possibility of using it to reduce the proportion of invasive diagnostic methods carried out in pregnant women for whom the result is negative in the end. By way of example, in the case of trisomy 21, which concerns one woman in 700, prenatal diagnosis is currently offered in France only if the mother is 38 years old, while a biochemical analytical test capable of detecting 60% of trisomy 21 cases for 5% of the price of amniocentesis is proposed for younger women. However, 40% of trisomy 21 cases are not detected by currently available tests. Prenatal detection of trisomy 21 in fetal cells isolated from the maternal plasma using a FISH technique has been described. That approach is interesting, but as fetal cells are rare in plasma (1 in 500 to 1 in 2000) and often include apoptotic cells, reliable diagnosis would require carrying out the method on a very large number of cells, rendering it impossible to carry out routinely. Further, euploid fetal cells cannot be identified by that approach.

One limitation of such approaches derives from the fact that fetal cells circulating in the blood are present in very low concentrations. Studies based on PCR detection of the Y chromosome in blood samples without prior selection have allowed the mean number of fetal cells to be determined to be about one fetal lymphocyte cell per milliliter of blood (Bianchi, *J Perinat Med* 1998 26: 175-85). More recently, the mean number of fetal cells has been revised upward as improved enrichment techniques yield more cells. One recent study found a mean value of 37 fetal lymphocytes per milliliter of blood. (Huang, *Prenatal Diagnosis* 2008 28: 892-899).

Thus, there is a need for improved methods and tools for detecting fetal alleles and fetal genetic variations.

SUMMARY OF THE INVENTION

Embodiments of the present invention relate to methods and genotyping panels for detecting fetal alleles and fetal genetic variations. One embodiment of the invention is a method of detecting a fetal identifier, comprising: obtaining a sample comprising a mixture of maternal and fetal cells; dividing the sample into subsamples; screening or genotyping a subsample for the presence of a fetal identifier; and identifying the presence of at least one fetal identifier from a fetal cell in at least one subsample.

Embodiments of the invention can and may comprise one or more of the following: a method further comprising performing subsample amplification on at least one subsample to provide an amplified product; a method further comprising dividing the amplified product into aliquots, where screening or genotyping a subsample for the presence of at least one fetal identifier comprises screening an aliquot for the presence of a fetal identifier; a method where subsample amplification comprises a method selected from the group consisting of: whole genome amplification, whole transcriptome amplification, targeted nucleic acid amplification, amplification of a nucleic acid sequence other than the fetal identifier, generation of a proxy for a nucleic acid sequence, and cell division; a method where preamplification comprises whole genome amplification or whole transcriptome amplification; a method where preamplification comprises targeted nucleic acid amplification, amplification of a nucleic acid sequence other than the fetal identifier, generation of a proxy for a nucleic acid sequence, and cell division; a method further comprising determining whether the genetic material of the maternal cells is homozygous or heterozygous at a set of target loci to determine a maternal genotype, where screening or genotyping an aliquot or subsample for a fetal identifier comprises screening or genotyping the aliquot or subsample for a genotype differing from the maternal genotype at least one target locus, where the presence of the genotype differing from the maternal genotype indicates the presence of an informative paternal allele in the amplified product, and where identifying the presence of at least one fetal identifier comprises identifying an informative paternal allele in at least one aliquot or subsample; a method further comprising selecting the target loci prior to determining whether the genetic material of the maternal cells is homozygous or heterozygous; a method further comprising selecting a test locus from the target loci, where screening comprises screening an aliquot for a genotype differing from the maternal genotype at the test locus; a method where selection of the test locus comprises screening a sample of mixed maternal and fetal nucleic acids for a genotype differing from the maternal genotype at a target locus, and selecting as the test locus a target locus with a non-maternal genotype in the sample of mixed maternal and fetal nucleic acids; a method further comprising analyzing an aliquot or subsample identified as containing the informative paternal allele to detect a genetic variation; a method further comprising collecting a portion of the aliquot or subsample identified as containing the informative paternal allele, where analyzing an aliquot or subsample identified as containing the informative paternal allele to detect a genetic variation comprises analyzing the collected portion of the aliquot or subsample; a method where the collected portion is a homogeneous portion of the aliquot or subsample; a method where the collected portion is a non-homogeneous portion of the aliquot; a method further comprising collecting an aliquot identified as containing the informative paternal allele from at least two subsamples and combining the aliquots prior to analyzing the amplified product; a method where the genetic variation is a fetal genetic variation selected from the group consisting of a chromosomal rearrangement, a copy number variation, and a polymorphism; a method where analysis comprises determining a ratio of maternally- and paternally-inherited alleles in an aliquot comprising the informative paternal allele, where the ratio is analyzed to determine the presence of a genetic variation; a method where analysis comprises determining a copy number of alleles in an aliquot comprising the informative paternal allele, where the copy number of alleles is analyzed to determine the presence of a genetic variation; a method further comprising analyzing an amplified product identified as containing the informative paternal allele from at least two the subsamples to detect the presence of mosaicism or dizygotic twins; a method where the analyzed aliquot or subsample is not the aliquot or subsample screened or genotyped for the presence of the fetal identifier, but is from the same subsample as the aliquot screened or genotyped for the presence of the fetal identifier; a method where the target loci are all homozygous for the maternal genotype, are all heterozygous for the maternal genotype, or comprise a mixture of homozygous and heterozygous loci for the maternal genotype; a method where the target loci are all homozygous for the maternal genotype; a method where the amplified product comprises genomic DNA or complementary DNA; a method where determining a maternal genotype comprises using a panel of SNPs to genotype a sample of maternal genetic material from the same individual that is the source of the maternal cells; a method where the source of the maternal genetic material is selected from the group consisting of blood, serum, plasma, urine, a cervical swab, tears, saliva, buccal swab, or skin; a method where the source of the maternal genetic material is selected from the group consisting of blood or a buccal swab; a method where the mixture of maternal and fetal nucleic acids is a mixture of cell-free nucleic acids; a method where the source of the maternal and fetal cell-free nucleic acid sample is blood, serum, plasma, urine, cervical swab, cervical lavage, uterine lavage, or culdocentesis from a pregnant female; a method comprising selecting and screening or genotyping more than one test locus in a single aliquot or subsample, selecting and screening or genotyping more than one test locus in more than one aliquot or subsample, or selecting and screening or genotyping one test locus in more than one aliquot or subsample; a method comprising selecting and screening or genotyping a second target locus in at least a second subsample following the identification of an informative paternal allele in a first aliquot or subsample; a method where the samples are divided to generate subsamples with a Poisson or a Non-Poisson distribution of cells; a method where each subsample comprises not more than one cell; a method further comprising pooling aliquots from two or more subsamples prior to screening or genotyping; a method where pooling comprises the use of an indexed system of rows and columns of wells comprising the aliquots; a method further comprising enriching the sample for the fetal cells prior to dividing into subsamples; a method where enriching comprises differential expansion of the fetal cells over the maternal cells; a method where a homogeneous portion of the amplified product is divided into the aliquots; and a method where a non-homogeneous portion of the amplified product is divided into the aliquots.

Yet another embodiment of the invention is a single nucleotide polymorphism (SNP) panel for detecting a fetal allele, comprising at least one chromosome-specific panel comprising about 5 to about 100 unique SNPs specific for a single chromosome, where each of the SNPs has a frequency in the range of about 30% to about 50% as measured across all major population groups; and where the total number of SNPs in the SNP panel is between about 5 and about 100 SNPs.

DETAILED DESCRIPTION OF THE PREFERRED EMBODIMENT

Embodiments of the present invention relate to methods and genotyping panels for detecting fetal alleles (i.e., non-maternal alleles/informative paternal alleles) and fetal genetic variations.

Embodiments of the present invention allow for detection of fetal alleles and fetal genetic variations regardless of the gender of the fetus and without requiring a paternal nucleic acid sequence to serve as a reference sample. By distinguishing fetal cells from maternal cells, preferably on a cell-by-cell basis, embodiments of the invention overcome resource constraints imposed by the low abundance of fetal cells in maternal blood and preserve the integrity of the fetal genome or transcriptome for more extensive analysis than currently available methods. In addition, by distinguishing fetal cells on a cell-by-cell basis, embodiments of the invention allow for the detection of mosaicism and dizygotic twins.

In a preferred embodiment of the invention, a maternal sample is genotyped to identify homozygous target loci that are subsequently genotyped to detect the presence of fetal heterozygous loci in a sample comprising fetal cells. It will be understood by one of skill in the art in any of the embodiments described herein that a maternal sample can alternatively be genotyped to identify heterozygous target loci that are subsequently genotyped to detect the presence of fetal homozygous loci in a sample comprising fetal cells. In some embodiments, a mixture of maternal and fetal cells is obtained and enriched to generate a sample concentrated for fetal cells relative to maternal cells. The concentrated sample is then divided into subsamples such that each subsample preferably comprises only one cell. Each of these subsamples is then amplified to produce an amplified product corresponding to each subsample, providing access to the genomes corresponding to cells. Amplified products are then divided to generate aliquots. These aliquots are then individually screened for a non-maternal allele at least one locus that was previously identified as homozygous in the maternal sample or genotyped at least one locus that was previously identified as heterozygous in the maternal sample, with detection of a heterozygous or homozygous genotype, respectively, indicating the presence of a non-maternal allele in the aliquot, and thus a fetal genome or transcriptome. Detecting a heterozygous genotype may be accomplished by screening for the non-maternal allele only at a selected locus. Further analysis is then performed on the corresponding unscreened aliquots to detect a fetal genetic variation, with at least one aliquot comprising a complete fetal genome or transcriptome.

In another preferred embodiment of the invention, a maternal sample is genotyped, a mixture of maternal and fetal cells is obtained, and the sample is concentrated for fetal cells and divided into subsamples as discussed above. A panel of at least one target locus at which the maternal sample is homozygous is selected for screening or genotyping of the subsamples. Each of the subsamples is individually screened or genotyped at least one of these loci, with detection of a heterozygous genotype again indicating the presence of a non-maternal allele in the subsample. Analysis of the ratio of alleles in the heterozygous subsamples is then performed to detect a fetal copy number variation.

As used herein, nucleic acid means a deoxyribonucleic acid (e.g., DNA, mtDNA, gDNA, or cDNA), ribonucleic acid (e.g., RNA or mRNA), or any other variant of nucleic acids known in the art.

As used herein, target locus means a genomic or transcriptomic locus at which a sample containing maternal genetic material has a detectable genotype. In some embodiments with more than one target locus, the target loci are comprised of all homozygous loci, all heterozygous loci, or a mixture of homozygous and heterozygous loci. The panel of target loci can also comprise all homozygous loci, all heterozygous loci, or a mixture of homozygous and heterozygous loci.

As used herein, test locus means a target locus selected for further genotyping in a sample comprising fetal genetic material.

As used herein, a fetal identifier refers to any indicator that a sample or portion thereof is fetal in origin. A fetal identifier can include any genetic variation or other information. One example of a fetal identifier is a fetal allele. As used herein, a fetal allele refers to a paternal allele that provides the ability to identify a genetic source as fetal. A paternal allele is any allele present in a paternal sample. However, as used herein, an informative paternal allele is any allele equivalent to a non-maternal allele (as used herein) or a fetal allele (as used herein).

As used herein, genetic variation means any variation in a nucleic acid sequence. Genetic variations can range from a single base pair variation to a chromosomal variation, or any other variation known in the art. Genetic variations can be simple sequence repeats, short tandem repeats, single nucleotide polymorphisms, translocations, inversions, deletions, duplications, or any other copy number variations. In some embodiments, the chromosomal variation is a chromosomal abnormality. For example, the chromosomal variation can be aneuploidy, inversion, translocation, a deletion, or a duplication. A genetic variation can also be mosaic. For example, the genetic variation can be associated with genetic conditions or risk factors for genetic conditions (e.g., cystic fibrosis, Tay-Sachs disease, Huntington disease, Alzheimer disease, and various cancers). Genetic variations can also include any mutation, chromosomal abnormality, or other variation disclosed in the priority documents (e.g., aneuploidy, microdeletions, or microduplications) cited above. Genetic variations can have positive, negative, or neutral effects on phenotype. For example, chromosomal variations can include advantageous, deleterious, or neutral variations. In some embodiments, the genetic variation is a risk factor for a disease or disorder. In some embodiments, the genetic variation encodes a desired phenotypic trait.

Obtain a Sample (e.g., Comprising a Mixture of Maternal and Fetal Cells)

The maternal samples, samples of mixed maternal and fetal cells, and samples of mixed maternal and fetal cell-free nucleic acids in embodiments of the invention can be obtained from blood. In some embodiments, about 20-40 mL of blood is drawn from a pregnant woman. Blood samples can be collected at any point during pregnancy. For example, in some embodiments, the maternal sample is collected during the first trimester. In other embodiments, the maternal sample is collected during the second trimester. In a preferred embodiment, blood is drawn at 10-18 weeks gestational age. However, blood can be drawn earlier in the pregnancy or after 18 weeks gestational age. The time of collection may vary depending on the information sought or the standards of prenatal care. Blood samples can also be collected at any time during the day. In some embodiments, blood is collected in the morning. In other embodiments, blood is collected in the afternoon.

Blood can be drawn from any suitable area of the body, including an arm, a leg, or blood accessible through a central venous catheter. In some embodiments, blood is collected following a treatment or activity. For example, blood can be collected following a pelvic exam. The timing of collection can also be coordinated to increase the number of fetal cells present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, or a DNA or RNA preservative following collection. In a preferred embodiment, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Maternal samples can also be obtained from other sources known in the art, including serum, plasma, urine, cervical swab, tears, saliva, buccal swab, skin, or other tissues. Samples of mixed maternal and fetal cells and samples of mixed maternal and fetal cell-free nucleic acids can also be obtained from other sources known in the art, including serum, plasma, urine, cervical swab, cervical lavage, uterine lavage, culdocentesis, lymph node, or bone marrow. For example, in some embodiments, the source of a sample of mixed maternal and fetal cell-free nucleic acids is a cervical swab. In a preferred embodiment, the fetal cell-free nucleic acids comprise DNA. In another embodiment, the fetal cell-free nucleic acids comprise RNA or cDNA.

Enrich for Fetal Cells

In order to address the low abundance of fetal cells in mixed samples of maternal and fetal cells, these samples can be enriched for fetal cells. Because red blood cells are enucleated when mature, but nucleated when immature, these properties can be used to differentiate maternal and fetal red blood cells in a sample. Samples can be enriched for fetal cells through positive selection, negative selection, or a combination of positive and negative selection. In some embodiments, fetal cells are directly captured. In other embodiments, maternal cells are captured and fetal cells are collected from the remaining sample.

Samples can be enriched for fetal cells based on differences in the physical properties of cells. For example, samples can be enriched for fetal cells based on density, cell membrane structure, or morphology. In some of the embodiments based on density, density gradients such as FICOLL™ (GE Healthcare Life Sciences, Piscataway, N.J.), PERCOLL™ (GE Healthcare Life Sciences, Piscataway, N.J.), iodixanol (Axis Shield, Oslo, Norway), NYCODENZ® (Axis Shield, Oslo, Norway), or sucrose are used. In some of the embodiments based on cell membrane structure, a lysis reagent (e.g., ammonium chloride) is used. In some of the embodiments based on morphology, flow cytometry or filters are used. Samples can also be enriched for fetal cells based on other physical properties known in the art. For example, samples can be enriched for fetal cells based on dielectric or magnetic properties. Further, samples can be enriched for fetal cells by collecting bone marrow.

Samples can also be enriched for fetal cells based on differences in the biochemical properties of cells. For example, samples can be enriched for fetal cells based on antigen, nucleic acid, metabolic, gene expression, or epigenetic differences. In some of the embodiments based on antigen differences, antibody-conjugated magnetic or paramagnetic beads in magnetic field gradients or fluorescently labeled antibodies with flow cytometry are used. In some of the embodiments based on nucleic acid differences, flow cytometry is used. In some of the embodiments based on metabolic differences, dye uptake/exclusion measured by flow cytometry or another sorting technology is used. In some of the embodiments based on gene expression, cell culture with cytokines is used. In some of the embodiments based on epigenetic differences, cell culture is used. Samples can also be enriched for fetal cells based on other biochemical properties known in the art. For example, samples can be enriched for fetal cells based on pH or motility. Further, in some embodiments, more than one method is used to enrich for fetal cells.

In some embodiments of the invention, samples are enriched for fetal cells by removing red blood cells through the use of lysis reagents such as ammonium chloride or by separation using density gradients such as FICOLL™ (Sigma-Aldrich, St. Louis, Mo.), PERCOLL™ (GE Healthcare Life Sciences Piscataway, N.J.), or sucrose. A density gradient can also be used to reduce the white cell fraction. The resulting peripheral blood mononuclear cells ("PBMCs") can be further enriched for fetal cells using magnetic bead separation techniques from manufactures such as Miltenyi Biotec (Gladbach, Germany), Stemcell Technologies (Vancouver, BC, Canada), and Dynal Biotech/Invitrogen (Carlsbad, Calif.). Positive enrichment or negative depletion or a combination of both can be used to enrich the fetal fraction in the PBMCs.

While no fetal specific surface markers are currently known, there are several markers that have been shown to positively enrich fetal cells to 1 fetal cell in 1,000 to 100,000 maternal cells. In some embodiments, CD71, CD34, CD45, or CD235a cell surface markers are used to enrich fetal cells. In some embodiments, cell surface markers that are not found on fetal cell populations are used to negatively enrich fetal cells by depleting adult cell populations. In some embodiments, combinations of CD2, CD3, CD11b, CD14, CD15, CD16, CD19, CD56, CD123 and CD61 are used to deplete adult cells. Flow cytometry sorting may also be used to further enrich for fetal cells using cell surface markers or intracellular markers conjugated to fluorescent labels. Intracellular markers may include nuclear stains or antibodies against intracellular proteins preferentially expressed in fetal cells (e.g., fetal hemoglobin).

Oxidation of hemoglobin has been identified as one way to preferentially enrich nucleated red blood cells (NRBCs) using magnetic field gradients (Zborowski, *Biophys J* 2003 84(4): 2638-2645). In addition, microfluidic devices have been developed which facilitate separation of red cells from white cells or enrich fetal cells from PBMCs (Huang, *Prenatal Diagnosis* 2008 28: 892-899).

In some embodiments of the invention, samples are enriched for fetal cells by differentially expanding fetal cells over maternal cells in culture. Differential expansion can be performed by any number of methods known in the art, including incubating cells from a sample of maternal blood containing CD34+ cells of both maternal and fetal origin in the presence of Stem Cell Factor (SCF) in serum free media as described in WO 2008/048931, which is herein incorporated by reference in its entirety.

In some embodiments of the invention, fetal cells in a mixture of maternal and fetal cells are enriched to about 1 in 2, about 1 in 5, about 1 in 10, about 1 in 100, about 1 in 1000, about 1 in 10000, or about 1 in 100000 fetal:maternal cells, or a range defined by any two of the preceding values.

Divide into Subsamples

Prior to subsample amplification (preferably using whole genome amplification (WGA) or whole transcriptome amplification (WTA)), screening or genotyping for homozygous or heterozygous loci, the samples can be divided into subsamples with few enough cells such that the chromosome copy number from the samples is preserved in the subsamples even following subsample amplification (e.g., WGA or WTA). Samples can be divided into subsamples consistent with a Poisson Distribution or a Non-Poisson Distribution. In some embodiments, samples are divided sequentially. For example, samples can be divided in serial. In other embodiments, samples are divided in parallel.

In some embodiments, samples are divided to provide subsample volumes of, less than, or less than about, 100 uL, 50 uL, 10 uL, 1000 nL, 500 nL, 400 nL, 300 nL, 200 nL, 100 nL, 50 nL, 30 nL, 10 nL, 3 nL, or 1 nL, or a range defined by any two of the preceding values. Preferably, each subsample contains a volume not more than 100 nL. In some embodiments, each subsample comprises not more than about 500, 400, 300, 200, or 100 cells, or a range defined by any two of the preceding values. Preferably, each subsample comprises not more than about 50, 40, 30, 20, or 10 cells, or a range defined by any two of the preceding values. More preferably, each subsample comprises not more than about 5, 4, 3, or 2 cells. In some embodiments, each subsample comprises not more than one cell.

In some embodiments, each subsample comprises an average of, or of about, 500, 400, 300, 200, or 100 cells, or a range defined by any two of the preceding values. Preferably, each subsample comprises an average of about 50, 40, 30, 20, or 10 cells, or a range defined by any two of the preceding values. More preferably, each subsample comprises an average of, or of about, 5, 4, 3, or 2 cells, or a range defined by any two of the preceding values. In some embodiments, each subsample comprises an average of less than about one cell, about one cell, or about one to two cells, or a range defined by any two of the preceding values.

The division of samples is performed by any method known in the art, including the use of oil plugs to create oil separation of individual cells in a microfluidic device, deposition into wells, or free-standing drops anchored by surface tension to a flat substrate. In addition, a subsample can be suspended in a buffer that will be appropriate for subsequent reactions. For example, a subsample can suspended in a solution comprising lysis and PCR buffers that will allow for a single-step cell lysis followed by amplification without further manipulation of subsamples.

Amplify Subsamples

To compensate for the limited amount of genetic material in a single cell or subsample, subsample amplification can optionally be performed. For example, nucleic acid replication or cell division can be performed. Samples are divided into subsamples with few enough cells such that the chromosome copy number from the samples is preserved in the subsamples following subsample amplification. In a preferred embodiment, subsample amplification is performed on a subsample containing a single cell, so that the resulting amplified product represents the genome or transcriptome of either a maternal or fetal cell. For example, subsample amplification can be performed on individual cells that are located in microwells or in drops separated by oil plugs as described herein.

Nucleic acid replication can be performed using any method for generating additional copies of nucleic acids, additional signals indicative of nucleic acids, or other proxies for nucleic acids (e.g., protein expression) known in the art. In some embodiments, nucleic acid replication is performed using WGA, WTA, or targeted nucleic acid amplification techniques. In other embodiments, nucleic acid replication is performed using methods that generate a signal indicative of nucleic acid sequences, such as INVADER® (Hologic, Inc., Bedford, Mass.). In some embodiments, only a portion of the amplified sequence is complementary to the nucleic acid template. For example, in some embodiments, a contiguous amplified product contains a portion of the nucleic acid template and a portion of a signal sequence. General techniques for nucleic acid replication can include isothermal or thermocycled replication. In some embodiments, nucleic acid replication is performed prior to SNP genotyping. However, nucleic acid replication can also be performed after SNP genotyping.

Cell replication can also be performed using any method known in the art. In some embodiments, cells are cultured in media and supplements to generate additional nucleic acid copies for use in the methods described herein. In other embodiments, cells are cultured and one or more cell is left intact for use in subsequent analysis. In some embodiments, cell replication is performed prior to division into subsamples. Preferably, cell replication is performed after division into subsamples.

Divide into Aliquots

Following subsample amplification, amplified products can be divided into aliquots. These aliquots can be used for a plurality of assays. For example, in one embodiment, one or more of the aliquots from an amplified product is used to detect the presence of a fetal allele, while one or more of the other aliquots is used to detect the presence of a fetal genetic variation in an amplified product that contains a fetal genome or transcriptome. In some embodiments, an aliquot identified as containing a fetal genome or transcriptome is assayed by array for genetic variations. For example, an aliquot can be assayed for genetic variations associated with genetic conditions (e.g., Williams syndrome, Wolf-Hirschhorn syndrome, Miller-Dieker syndrome, Smith Magenis syndrome, Angelman syndrome, Di George syndrome, Prader-Willi syndrome, Jacobsen syndrome, Cri du chat syndrome, Charcot-Marie-Tooth disease, microduplication 22q11.2 syndrome, cystic fibrosis, Tay-Sachs disease, Huntington disease, Alzheimer disease, and various cancers).

Homogenous or non-homogeneous portions of amplified products can be selected for division into aliquots. In some embodiments, homogenous portions of amplified products are divided sequentially (e.g., in serial). In other embodiments, homogeneous portions of amplified products are divided in parallel. Alternatively, non-homogeneous portions of amplified products can be selected for division into aliquots using positive selection, negative selection, or a combination of positive and negative selection. For example, in some embodiments, bead-bound capture oligos are used to target desired portions of amplified products for division into aliquots. In other embodiments, surface-bound oligos are used to eliminate undesired portions of amplified products. Non-homogeneous portions of amplified products can be selected based on any physical or biochemical property known in the art, including those described herein. For example, portions of amplified products with a particular charge, size, or chromosomal identity can be selected for division into aliquots.

In some embodiments where the optional step of subsample amplification is not carried out, a portion or aliquot of a subsample can be removed for subsequent analysis.

In some embodiments, aliquots are pooled into groups of two or more aliquots. This allows the number of SNP-based or other reactions described herein to be reduced by as much as a factor of N, where N is the number of aliquots in each pool. Aliquots from positive pools (i.e., pools with at least one genotype differing from the maternal genotype) may then be retested aliquot-by-aliquot to identify the aliquot containing a fetal allele. In some embodiments, each pool is tested for a non-maternal allele at a test locus. In some embodiments, each pool is tested for non-maternal alleles at two or more test loci.

In some embodiments, aliquots are pooled using an indexing system that allows for identification of the source of a positive aliquot within a positive pool. For example, two or more aliquots may be taken from each amplified product to form indexed pools of N×M amplified aliquots. Wells containing at least one fetal allele can be identified by locating the intersection of positive N and M pools in the orthogonal ordinate system. In some embodiments, N (i.e., the number of columns in the N×M index) and M (i.e., the number of rows in the N×M index) are independently between about 2 and about 1000. Preferably, N and M are independently between about 8 and about 100. In some embodiments, N is, is about, is at least, is at least about, is not more than, is not more than about 2, 3, 4, 5, 6, 7, 8, 9, 10, 11, 12, 13, 14, 15, 16, 17, 18, 19, 20, 21, 22, 23, 24, 30, 32, 36, 40, 48, 50, 56, 60, 64, 70, 72, 80, 84, 88, 90, 96, 100, 192, 288, 384, 480, 576, 672, 768, 864, 960, 1000, or a range defined by any two of the preceding values. In some embodiments, M is, is about, is at least, is at least about, is not more than, is not more than about 2, 3, 4, 5, 6, 7, 8, 9, 10, 11, 12, 13, 14, 15, 16, 17, 18, 19, 20, 21, 22, 23, 24, 30, 32, 36, 40, 48, 50, 56, 60, 64, 70, 72, 80, 84, 88, 90, 96, 100, 192, 288, 384, 480, 576, 672, 768, 864, 960, 1000, or a range defined by any two of the preceding values. In preferred embodiments, homogeneous or non-homogeneous portions of amplified products are indexed to allow for identification of the source of positive aliquots.

Obtain or Infer a Parental Genotype

Parental genotypes can be obtained or inferred to aid in the identification of non-maternal alleles. Information regarding non-maternal alleles can in turn be used to screen or genotype aliquots or subsamples, or to directly analyze fetal genomes for genetic variants. For example, paternal or maternal genotypes can be obtained by directly genotyping paternal or maternal samples, or inferred by genotyping samples from genetically related family members. However, in a preferred embodiment, there is no need to obtain or infer a paternal genotype. For example, in a preferred embodiment, only a maternal genotype is obtained.

In some embodiments, paternal or maternal genotypes are obtained by genotyping genetic material from blood, plasma, serum, urine, buccal swab, saliva, tears, skin, or any other source of paternal nucleic acids (including those described herein). In some embodiments, paternal or maternal genotypes are obtained using cell-free nucleic acids or nucleic acids extracted from cells derived from one of these sources. Paternal or maternal genotyping is also preferably performed on DNA, but can also be performed on RNA, cDNA, or any other nucleic acid known in the art. In some embodiments, the template of a paternal or maternal sample is amplified and detected (e.g., using PCR-based methods). However, in some embodiments, the template of a paternal or maternal sample is not amplified (e.g., using the methods described herein).

Paternal and maternal genotypes can also be obtained by accessing information generated during prior genetic testing, such as information in a database, in a test report, or from a previous pregnancy for which a method described herein was performed. Paternal or maternal genotypes can also be inferred using the genotypes of blood relatives. For example, the genotypes of genetically related parents, siblings, grandparents, aunts, uncles, or children can be used to infer a paternal or maternal genotype.

Any polymorphism known in the art can be used to genotype a parental sample. For example, SNPs, haplotypes, short tandem repeats (STRs), or other sequence variations can be genotyped. Other genetic or epigenetic markers can also be used to genotype a parental sample. For example, copy number variations (CNVs) or methylation patterns can be assessed.

Optionally Identify at Least One Non-Maternal Allele in a Mixture of Maternal and Fetal Nucleic Acids In embodiments where a homozygous target locus has been identified in a maternal sample, a mixture of maternal and fetal nucleic acids can optionally be used to identify a heterozygous genotype at the same locus, which indicates the presence of a fetal (i.e., non-maternal allele/informative paternal allele). This optional step is preferably performed prior to screening or genotyping the individual aliquots or subsamples. By screening for a non-maternal allele, and thereby identifying a heterozygous locus (and therefore a fetal allele) in the mixed sample of maternal and fetal nucleic acids, the aliquots and subsamples can be more efficiently screened for SNPs that are known to be informative. In a preferred embodiment, fetal cell-free DNA is used to screen for the non-maternal allele and identify the heterozygous locus. In another embodiment, fetal cell-free RNA or cDNA is used to identify the heterozygous locus.

Cell-free nucleic acids can be obtained from any source known in the art, including blood, serum, plasma, urine, cervical swab, cervical lavage, uterine lavage, or culdocentesis from a pregnant woman. Nucleic acids can also be extracted from a mixed sample of maternal and fetal cells to identify the heterozygous locus. Preferably, DNA is extracted from a mixed sample of maternal and fetal cells. However, RNA or cDNA can be extracted from a mixed sample of maternal and fetal cells. Nucleic acids can be extracted from cells obtained from any source known in the art, including blood, cervical swab, cervical lavage, uterine lavage, culdocentesis, lymph node, or bone marrow. In other embodiments, whole blood is used to identify a heterozygous genotype without (or prior to) dividing the whole blood into a cellular, plasma, or serum fraction.

In some embodiments, the nucleic acid template of an aliquot from a mixed sample of maternal and fetal nucleic acids is amplified and detected to identify a heterozygous locus (e.g., using PCR-based methods). However, in some embodiments, the nucleic acid template of an aliquot from a mixed sample is not amplified to identify a heterozygous locus. For example, methods in which only a signal associated with the template is amplified (e.g., the ABSCRIPTION™ method as described in U.S. Pat. Nos. 7,226,798, 7,473,775, and 7,468,261 (Ribomed Biotechnologies, Inc., Carlsbad, Calif.) or methods involving the INVADER® chemistry (Hologic, Inc.)) can be employed. Methods in which the nucleic acid template is detected without amplification of the signal or the template (e.g., the method involving chemical detection of DNA binding as described in WO 2005/01122 (Adnavance Technologies, Inc., San Diego, Calif.)) can also be employed. In addition, methods in which the nucleic acid template is sequenced without amplification (e.g., the sequencing method as described in Eid et al., *Science* 2009 323(5910): 133-38) can be employed. It will be understood by one of skill in the art that the source of the template for the identification of a non-maternal allele can include serum, plasma, urine, a cervical swab, or any other source of nucleic acids known in the art.

Screen or Genotype at Least One Aliquot or Subsample for the Presence of at Least One Informative Paternal Allele The next steps are to screen or genotype subsamples or aliquots to identify non-maternal alleles. Once a SNP panel has been generated (as described in more detail herein) and a set of target loci for which the maternal genetic sample is homozygous (or, alternatively, heterozygous) has been identified, a test locus or loci can be selected to screen or genotype the subsample or aliquot for the presence of a fetal allele. To detect the presence of a fetal allele, a test locus is screened or genotyped for the presence of a non-maternal allele (i.e., by identifying a heterozygous, or alternatively homozygous genotype at the test locus). In some embodiments, aliquots of an amplified product are screened or genotyped aliquot-by-aliquot to detect a heterozygous (or, alternatively, homozygous) locus. In some embodiments, an aliquot contains amplified material from a single cell.

A subsample or aliquot can be genotyped at a locus previously identified as homozygous in a maternal sample. In some embodiments, the genotype at a locus previously identified as homozygous in a maternal sample is determined by screening for the presence of a non-maternal allele. Optionally, as described herein, prior to screening the aliquots or subsample for the non-maternal allele, a sample of mixed maternal and fetal nucleic acids (preferably cell-free) was used to identify the presence of a non-maternal allele in the mixed nucleic acid, indicating the presence of a heterozygous genotype at the same locus in the fetal material.

In other embodiments, a subsample or aliquot is genotyped at a locus previously identified as heterozygous in a maternal sample. The identification of a homozygous genotype in the aliquot or subsample for the same locus indicates the presence of a non-maternal, i.e., fetal allele.

It will be understood by one of skill in the art that the screening or genotyping methods in any of the embodiments described herein may be performed using either aliquots or subsamples. Aliquots and subsamples can be screened or genotyped for a fetal allele using a number of methods known in the art, including those mentioned herein. For example, aliquots can be screened or genotyped using molecular beacons or other nucleic acid-based SNP detection methods. In some embodiments, the nucleic acid template in an aliquot is amplified and detected (e.g., using PCR-based methods). However, in some embodiments, the nucleic acid template is not amplified (e.g., using the methods described herein). Further, any marker known in the art can be used to screen or genotype aliquots and subsamples. In preferred embodiments, the SNP, haplotype, short tandem repeat (STR), other sequence variation, copy number variation (CNV), or epigenetic marker genotyped in the maternal sample is used.

Because in some embodiments subsamples comprise not more than one cell, the screening or genotyping of a subsample or aliquot can be cell-by-cell. Subsamples or aliquots can also be screened or genotyped using a number of methods known in the art, including those mentioned herein. Preferably, subsamples are screened for heterozygous alleles using quantitative PCR (qPCR) with a TAQMAN® system (Foster City, Calif.). A predetermined number of subsamples or cells can be screened to detect a heterozygous allele. For example, as shown in Table 1, to test 7 loci in a sample enriched to 1:10,000 fetal:maternal cells, where approximately 5 fetal cells per loci are expected, the predetermined number of samples or cells is 350,000. In some embodiments, the number of fetal cells per loci is, is about, is at least, is at least about, is not more than, is not more than about 1, 2, 3, 4, 5, 6, 7, 8, 9, 10, 15, 20, 25, 30, 35, 40, 50, 60, 70, 80, 90, 100, 125, 150, 175, 200, 225, 250, 275, or 300, or a range defined by any two of the preceding values.

maternal allele. If a non-maternal allele is not detected, additional test loci are screened or genotyped until the number of test loci run exceeds a designated cumulative probability of detecting a non-maternal (and therefore fetal) allele from a mixed sample.

Test loci can also be screened or genotyped until more than one fetal allele is detected. If more than one test locus is screened or genotyped, each additional locus testing positive for a fetal allele (i.e., with a genotype differing from the maternal genotype) increases the confidence of detecting a fetal genome in a subsample or aliquot. In addition, a predetermined number of test loci can be designated to account for the fact that fetal genetic material may not be present. In some embodiments, a predetermined number of test loci is determined by calculating the cumulative probability of detecting a fetal allele for a relevant set of variables. For example, as shown in Table 3, the probability of detecting the presence of a heterozygous fetal allele using 7 SNPs with a minor allele frequency of about 0.5 is $1-(0.5)(0.5)(0.5)(0.5)(0.5)(0.5)(0.5)=99.22\%$. As shown in Table 1, for 350,000 aliquots or subsamples from a sample enriched for 1:10,000 fetal:maternal cells, the predetermined number of test loci can therefore be about 7 test loci.

Test loci can be screened or genotyped individually or in multiples. In some embodiments, one test locus is screened or genotyped in a single aliquot or subsample. A single test locus can also be screened or genotyped in multiple aliquots or subsamples. In addition, aliquots or subsamples can be screened or genotyped individually or in multiples. In some embodiments, more than one test locus is screened or geno-

TABLE 1

| | | Total Enriched Cells (in Thousands) | | | | | | | |
|---|---|---|---|---|---|---|---|---|---|
| | | 50 | 100 | 150 | 200 | 250 | 300 | 350 | 400 |
| | | Number of loci possible with 5 fetal cells per loci | | | | | | | |
| Fetal | 1:100 | 100 | 200 | 300 | 400 | 500 | 600 | 700 | 800 |
| Frequency | 1:1,000 | 10 | 20 | 30 | 40 | 50 | 60 | 70 | 80 |
| | 1:10,000 | 1 | 2 | 3 | 4 | 5 | 6 | 7 | 8 |

Identify at Least One Informative Paternal Allele in at Least One Aliquot or Subsample As described herein, after homozygous (or, alternatively, heterozygous) SNPs are identified in maternal genetic material, these SNPs can be screened or genotyped in the subsamples or aliquots to detect the presence of a non-maternal allele. If a first maternal homozygous/heterozygous SNP does not generate a heterozygous/homozygous genotype in the aliquots or subsamples, a second maternal homozygous/heterozygous SNP can be selected and genotyped. This process can be repeated until a non-maternal allele is detected or until a predetermined number of SNPs and/or cells, subsamples or aliquots are screened. The process can also involve genotyping multiple aliquots or subsamples, multiplexing SNPs, or any combination thereof.

Test loci are screened or genotyped such that at least one fetal allele will be detected if present in a sample. In some embodiments, test loci are screened or genotyped until at least one non-maternal allele is detected. In some embodiments, a first test locus is screened or genotyped in aliquots or subsamples until enough cells are genotyped to exceed a designated probability of detecting a non-maternal allele. If a non-maternal allele is not detected, a second test locus is screened or genotyped in aliquots or subsamples until enough cells are run to exceed a designated probability of detecting a nontyped in a single aliquot or subsample. In addition, more than one test locus can also be screened or genotyped in multiple aliquots or subsamples. In some embodiments, the number of test loci in a panel is, is about, is at least, is at least about, is not more than, is not more than about 2, 3, 4, 5, 6, 7, 8, 9, or 10 test loci multiplexed to screen for or genotype a fetal allele, or a range defined by any two of the preceding values.

In some embodiments, a locus identified as containing a heterozygous (and therefore non-maternal) genotype in a mixture of maternal and fetal nucleic acids (preferably cell-free) is screened subsample-by-subsample with subsamples derived from a mixture of maternal and fetal cells. Conserved aliquots and subsamples can then be used to perform additional genetic analyses. However, despite the advantages of maternal and fetal cell-free nucleic acids in detecting the presence of a fetal allele, these samples are not suitable for analyses that require preservation of the integrity of the fetal genome or transcriptome, or capture of samples. This highlights one of the benefits of using the cell-based methods described herein.

Collect Aliquots or Subsamples

Aliquots or subsamples identified as containing a fetal allele can be collected for subsequent analyses. The aliquot(s) collected for subsequent analysis can be the same one(s) used to screen for the fetal allele, or a different aliquot from the same subsample can be used to provide an aliquot that has not be subject to any reactions used for fetal allele screening. In some embodiments, aliquots or subsamples are selected for collection based on quality, quantity, or the presence of desired nucleic acids. For example, aliquots or subsamples can be selected for collection using signal correlations, signal intensities, signal intensity ratios, signals compared to a background measurement, assay kinetics plotted against time, assay kinetics plotted against temperature, or other performance metrics known in the art. In some embodiments, the marker or region used to discriminate paternal from maternal alleles is collected. However, in other embodiments, an unlinked marker or region is collected for further analysis.

In some embodiments, only a desired portion of an aliquot or subsample is collected for subsequent analysis. For example, in some embodiments, a hybridization probe is used to collect only nucleic acid sequences from a chromosome or region of interest. In other embodiments, an entire aliquot, subsample, or a homogenous portion thereof is collected.

Analyze at Least One Fetal Genome for Genetic Variants

Aliquots or subsamples identified as having a non-maternal allele, optionally collected as described herein, can be further analyzed, for example, to test for the presence of a chromosomal or genetic variation. The aliquot used for analysis can be the same one screened or genotyped for the fetal allele. Or the aliquot used for analysis can be a different aliquot from the same subsample, but one that was not subject to any screening or genotyping for a fetal allele. Entire fetal genomes or portions thereof can be selected for further analyses. In some embodiments, polymorphisms are genotyped using methods known in the art. For example, SNPs, haplotypes, or STRs can be genotyped using PCR and, if appropriate, subsequent detection methods such as capillary electrophoresis. Polymorphisms can also be genotyped using sequencing methods. Genotyping is preferably performed using high throughput techniques. For example, in some embodiments, a microarray is used to generate data regarding SNPs and/or haplotypes. Copy number variation can also be assessed for further analyses. For example, array comparative genomic hybridization (aCGH) can be used to detect copy number variations. Chromosomal rearrangements can also be assessed. For example, inversions or translocations can be detected using methods such as sequencing, FISH, or PCR.

In some embodiments, a ratio of maternally- and paternally-inherited alleles is determined to analyze the presence of a genetic variation. Optionally, the same locus is used to determine the presence of a fetal allele and the presence of a genetic variation. For example, intensity of the alleles at a heterozygous test locus can be measured, with a 2:1 or 1:2 intensity ratio indicating copy number variation. However, in some embodiments, the locus used to determine the presence of a fetal allele is not the same locus used to determine a genetic variation. In addition, it will be understood by one of skill in the art in any of the embodiments described herein that other intensity ratios (e.g., 3:1, 1:3, 3:2, 2:3, 4:1, and 1:4) can be used to detect the presence of copy number variation.

In some embodiments, an overrepresentation or underrepresentation of chromosomal sequences is determined to analyze the presence of copy number variation. For example, the number of unique sequence reads for a particular chromosome can be measured and compared to a maternal and/or other reference chromosome, with a ratio less than or greater than 1:1 indicating a copy number variation. The detection of these unique sequence reads can be performed using small scale (e.g., sequencing with primer pairs designed for specific loci) or large scale (e.g., sequencing of the entire genome) methods. The number of sequence reads for a particular chromosomal region can also be measured and compared to a maternal and/or other reference chromosomal region, with a ratio less than or greater than 1:1 indicating the presence of a copy number variation.

Aliquots or subsamples may be analyzed individually or in a combined sample of at least two aliquots or subsamples. In some embodiments, aliquots or subsamples are ranked based on signal metrics as described herein and a preferred set is selected for analysis or pooling followed by analysis. In some embodiments, isolated aliquots or subsamples or pools are tested for the presence of a genetic or chromosomal variation using array comparative genomic hybridization (aCGH), quantitative fluorescence PCR (QF-PCR), short tandem repeat (STR) analysis, or sequencing. However, any technique known in the art, including those described herein, can be used to test for the presence of a genetic or chromosomal variation.

Screening or genotyping aliquots or subsamples on a cell-by-cell basis allows for the detection of mosaicism (i.e., a condition in which cells from the same individual have different genetic profiles). For example, subsamples can be screened or genotyped to detect a mosaic chromosomal variation. In some embodiments, the number of subsamples screened or genotyped for mosaicism is about 2 to about 100 subsamples. In some embodiments, the number of subsamples screened or genotyped is, is about, is at least, is at least about, is not more than, is not more than about 2, 3, 4, 5, 6, 7, 8, 9, 10, 15, 20, 25, 30, 35, 40, 50, 60, 70, 80, 90, or 100, or a range defined by any two of the preceding values. In a preferred embodiment, the number of subsamples screened or genotyped is about 5 to about 10 subsamples. Optionally, the same locus is used to determine the presence of a fetal allele and the presence of mosaicism. For example, intensity of the alleles at a heterozygous test locus can be measured, with a 1:1 intensity ratio in at least one subsample and a 2:1 or 1:2 intensity ratio in at least one other subsample indicating the presence of a mosaic genetic variation. However, different loci can also be used to determine the presence of a fetal allele and the presence of mosaicism. For example, a homozygous test locus can be used to identify a fetal allele. A heterozygous locus can then be detected and the intensity of the alleles at the heterozygous locus can be measured, with a 1:1 intensity ratio in at least one subsample and a 2:1 or 1:2 intensity ratio in at least one other subsample again indicating the presence of a mosaic genetic variation.

In some embodiments, mosaicism is detected using a sex-specific chromosome. For example, alleles at a heterozygous X chromosome test locus can be detected, with the presence of one allele in at least one subsample and the presence of both alleles in at least one other subsample indicating the presence of mosaic aneuploidy (e.g., mosaic Turner syndrome). In another example, the presence of alleles at a homozygous X chromosome test locus can be detected, with a 1:1 X:Y chromosome intensity ratio in at least one subsample and a 2:1 X:Y chromosome intensity ratio in at least one other subsample indicating the presence of a mosaic aneuploidy (e.g., mosaic Klinefelter syndrome).

Screening or genotyping aliquots or subsamples on a cell-by-cell basis also allows for the detection of dizygotic twins (i.e., non-identical twins). For example, SNP genotyping can be performed on subsamples containing a fetal allele, with the presence of at least two subsamples with different SNP genotypes indicating the presence of dizygotic twins. In some embodiments, the number of SNPs screened or genotyped to detect dizygotic twins is about 1 to about 20 SNPs. In some embodiments, the number of SNPs screened or genotyped is, is about, is at least, is at least about, is not more than, is not more than about 1, 2, 3, 4, 5, 6, 7, 8, 9, 10, 11, 12, 13, 14, 15, 16, 17, 18, 19, or 20 SNPs, or a range defined by any two of the preceding values. In a preferred embodiment, the number of SNPs screened or genotyped is about 3 to about 4 SNPs. The probability of detecting the presence of dizygotic twins using 3 SNPs is about 1−(0.5)(0.5)(0.5)=87.5%, while the probability of detecting the presence of dizygotic twins using 4 SNPs is about 1−(0.5)(0.5)(0.5)(0.5)=93.75%, respectively.

In some embodiments, aliquots containing fetal alleles from dizygotic twins can be pooled. For example, aliquots comprising cells from a first twin can be pooled independently of aliquots comprising cells from a second twin. In some embodiments, pooled aliquots from a first and second twin can be independently placed on one or more arrays and assessed for genetic or chromosomal variation as described herein.

Techniques

Even if fetal DNA or RNA is present in a minor fraction of a sample comprising maternal and fetal genetic material, it is still possible to detect fetal SNP alleles using standard SNP detection formats, such as TAQMAN® PCR. However, to detect minor alleles, it may be necessary to optimize fluorescence detection to prevent maternal signal overlap from obscuring a fetal-specific signal. In some embodiments, optimal fluorescence dyes for probe labeling are selected to minimize overlap. For example, dyes separated across the standard fluorescence spectrum (400-700 nm) with less than 10% overlap between emissions can be selected. In this way, even minor signals (less than 10% signal intensity) from fetal alleles are not obscured by maternal signal (90% signal intensity). In some embodiments, optimal fluorescence filters are chosen to minimize overlap in emission detection and custom fluorescence detection hardware and software are chosen to minimize signal crosstalk. In some embodiments, digital PCR is used to optimize signal to background ratios.

Other potential tools for measuring allelic intensity include S-curve fitting and other statistical analyses known in the art. In some embodiments, Ct shift is measured to detect a genetic or chromosomal variation. For example, encapsulation of single cells for detection of fetal SNPs with TAQMAN® chemistry can allow for simultaneous detection of abnormal copy number for the SNP detected, and therefore the copy number of the corresponding chromosome. If a SNP resides on chromosome 21, the SNP abundance will correlate with a Ct value, and therefore a copy number for Chromosome 21. If a reaction contains a single cell, then the copy number of a chromosome in that cell can be detected by Ct shift. In this example, the use of the abundance of normal maternal cell Ct values establishes the Ct for a normal copy number of two chromosomes per cell and a Ct shift to an earlier cycle would indicate the presence of a copy number variation.

As described herein, sequencing methods can be used to screen for fetal alleles and/or to determine the presence of a genetic or chromosomal variation. In some embodiments, shotgun sequencing may be used as an alternative to CGH arrays to detect copy number variations (e.g., resulting from a genetic variation) as described, for example, in Xie and Tammi, *BMC Bioinformatics* 2009, 10(80). In some embodiments, whole genome sequencing may be performed.

SNP genotyping can also be performed using any method known in the art, including qPCR and TAQMAN® methods. A variety of SNP chemistries and platforms are available from manufacturers such as Life Technologies (TAQMAN®) (Carlsbad, Calif.), Illumina (GOLDENGATE®) (San Diego, Calif.), Millipore (AMPLIFLUOR®) (Billerica, Mass.), and DxS Ltd. (SCORPIONS™) (Manchester UK). Miniaturized formats are also available from BioTrove (OPENARRAY™) (Woburn, Mass.) and Fluidigm (BIOMARK™) (South San Francisco, Calif.).

SNP Panels

A SNP panel can be used to identify target loci in a maternal genetic sample. Once these target loci are identified, they are used to identify the presence of a non-maternal allele in a mixed sample. Because genotyping a maternal genetic sample to identify a target locus is expensive and time consuming, a SNP panel is designed to include as few SNPs as possible. However, the panel must still include enough SNPs to identify a large enough set of target loci to allow for the detection of a fetal allele in a mixed sample, with these SNPs being sufficiently informative to conserve the finite quantity of cells in a mixture of fetal and maternal cells.

The size of a SNP panel is inversely related to the minor allele frequencies of the SNPs in the panel. In some embodiments of the invention, the goal is to identify about 1 to about 5 fetal cells from a mixed sample of maternal and fetal cells. The number of SNPs that must be assessed to achieve this goal depends on the minor allele frequency of SNPs that are assessed and the number of cells that are genotyped. The number of cells that must be assessed, in turn, depends on the extent of enrichment of the mixed sample for fetal cells.

In some embodiments, a SNP panel is therefore designed to minimize the number of tests necessary to identify loci which are homozygous (or, alternatively, heterozygous) in a maternal sample and heterozygous (or, alternatively, homozygous) in a mixed sample of maternal and fetal genetic material. In some embodiments, a SNP panel is designed to identify about 1 to about 20 homozygous maternal SNPs per chromosome-specific SNP panel. In some embodiments, the SNP panel is designed to detect a number of homozygous maternal SNPs per chromosome-specific panel that is, is about, is at least, is at least about, is not more than, is not more than about 1, 2, 3, 4, 5, 6, 7, 8, 9, 10, 11, 12, 13, 14, 15, 16, 17, 18, 19, or 20 SNPs, or a range defined by any two of the preceding values. In a preferred embodiment, a SNP panel is designed to identify about 5 to about 10 homozygous maternal SNPs per chromosome-specific SNP panel. More preferably, a SNP panel is designed to identify about 7 homozygous maternal SNPs per chromosome-specific SNP panel. For example, as shown in Table 2, for SNPs in HWE where $p^2=0.25$, a panel of 20 SNPs is needed to identify 10 SNPs for which the maternal sample is homozygous.

Several chromosome-specific SNP panels, preferably comprising at least one control chromosome-specific panel, can be combined to create a SNP panel for genotyping maternal genetic material. Each chromosome-specific panel is designed to generate a target set of loci for that chromosome. Preferably, a chromosome-specific SNP panel comprises about 5 to about 100 unique SNPs. Preferably, the total number of SNPs in a chromosome-specific panel is between about 5 and about 30 unique SNPs. More preferably, the total number of SNPs in a chromosome-specific panel is about 20 SNPs. In some embodiments, the total number of SNPs in a chromosome-specific panel is, is about, is at least, is at least about, is not more than, is not more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100 SNPs, or a range defined by any two of the preceding values.

SNP panels may contain one or more chromosome-specific panels. A chromosome-specific SNP panel can comprise SNPs located on autosomal chromosomes, preferably SNPs located on chromosomes that are susceptible to aneuploidy in clinical relevant syndromes. More preferably, chromosome-specific SNP panels comprise SNPs located on Chromosome 13, 18, 21, X, and Y. A chromosome-specific panel can also be a control chromosome-specific panel. Preferably, a control chromosome-specific panel comprises SNPs located on a chromosome that is not susceptible to aneuploidy or where the aneuploidy is incompatible with viability, which is typically the larger chromosomes that are designated by lower indices (e.g., chromosome 1, 2, or 3). Most preferably, a control chromosome-specific panel comprises SNPs located on Chromosome 1, 2, or 3. In addition, a chromosome-specific SNP panel can also comprise SNPs located on sex-specific chromosomes. In some embodiments, a panel is not specific for a particular chromosome. In some embodiments, the control is not a chromosome-specific SNP panel. For example, primers can be used to amplify a chromosome-specific region which will serve as a control.

In some embodiments, a SNP panel comprises more than one chromosome-specific panel, where the chromosome-specific panels are for SNPs on Chromosome 1, 2, 3, 4, 5, 6, 7, 8, 9, 10, 11, 12, 13, 14, 15, 16, 17, 18, 19, 20, 21, 22, X, or Y. In some embodiments, the SNP panel comprises 1, 2, 3, 4, 5, 6, 7, 8, 9, 10, 11, 12, 13, 14, 15, 16, 17, 18, 19, 20, 21, 22, or 23 chromosome-specific panels, or a range defined by any two of the preceding values. In some embodiments, the total number of SNPs in the panel is N*the number of SNPs on a chromosome-specific panel, where N is the number of chromosome-specific panels in the SNP panel.

Several factors can be considered in the selection of loci for genotyping panels. For example, Hardy-Weinberg equilibrium ("HWE") can be assumed to calculate probabilities of SNP allele frequencies. In some embodiments, the probability of the alleles in the selected SNPs is given by the following equation: $p^2+2pq+q^2=1$. For example, SNPs with a heterozygosity of 0.5 can be selected. HWE is preferred, as SNPs that are not in HWE are unlikely heritable SNPs, limiting their utility, or may result from faulty genotyping chemistry.

SNPs with one allele favored in homozygosity across major known haplotypes can also be selected. In some embodiments, SNPs with a homozygous maternal genotype (pp or qq) at less than 0.25 and an opposite homozygous genotype at more than 0.25 are selected.

In some embodiments, SNPs have a frequency in the range of about 30% to about 50% for the minor allele as measured across all major population groups. In a preferred embodiment, SNPs have a frequency in the range of about 49% to about 50% for the minor allele. In some embodiments, SNPs have a frequency that is, is about, is at least, is at least about, is not more than, is not more than about 30%, 31%, 32%, 33%, 34%, 35%, 36%, 37%, 38%, 39%, 40%, 41%, 42%, 43%, 44%, 45%, 46%, 47%, 48%, 49%, or 50% for the minor allele, or a range defined by any two of the preceding values.

Embodiments of the Invention

One embodiment of the invention is a method of detecting a fetal allele, comprising: obtaining a sample comprising a mixture of maternal and fetal cells; enriching the sample for fetal cells; dividing the enriched sample into subsamples; performing whole genome amplification on a subsample to provide an amplified genomic product; dividing the amplified genomic product into aliquots; identifying target loci at which the genetic material of the maternal cells is homozygous for a minor allele; selecting a test locus from the target loci; screening an aliquot for a non-maternal allele (heterozygous genotype) at the test locus, where the presence of the non-maternal allele (heterozygous genotype) indicates the presence of a fetal allele in the amplified genomic product; and identifying at least one fetal allele.

Another embodiment of the invention is a method of detecting a fetal genetic variation, comprising: a method of identifying a fetal allele in a mixed sample of maternal and fetal cells, comprising: obtaining a sample comprising a mixture of maternal and fetal cells; enriching the sample for fetal cells; dividing the enriched sample into subsamples, each subsample comprising not more than one cell; identifying a panel of at least one locus at which the genetic material of the maternal cells is homozygous for a minor allele; selecting a test locus from the target loci; screening a subsample for a non-maternal allele (heterozygous genotype) at a test locus selected from the panel, where the presence of the non-maternal allele (heterozygous genotype) indicates the presence of a fetal allele in the subsample; and identifying at least one fetal allele; and determining a ratio of maternally- and paternally-inherited alleles in a subsample comprising the fetal allele, where the ratio is analyzed to determine the presence of a genetic variation.

Another embodiment of the invention is a method of detecting a fetal allele, comprising: obtaining a sample comprising a mixture of maternal and fetal cells; dividing the sample into subsamples; performing preamplification on a subsample to provide an amplified product; dividing the amplified product into aliquots; selecting target loci and determining whether the genetic material of the maternal cells is homozygous or heterozygous at a set of target loci to determine a maternal genotype; selecting a test locus from the target loci; screening an aliquot for a genotype differing from the maternal genotype at the test locus, where the presence of a genotype differing from the maternal genotype indicates the presence of a fetal allele in the amplified product; and identifying at least one fetal allele.

Another embodiment of the invention is a method of detecting a fetal allele, comprising: obtaining a sample comprising a mixture of maternal and fetal cells; dividing the sample into subsamples; identifying a panel of at least one target locus and determining whether the genetic material of the maternal cells is homozygous or heterozygous for at least one target locus to determine a maternal genotype; selecting a test locus from at least one target locus; screening a subsample for a genotype differing from the maternal genotype at the test locus selected from the panel, where the presence of a genotype differing from the maternal genotype indicates the presence of a fetal allele in the subsample; and identifying at least one fetal allele.

Embodiments of the invention can and may comprise one or more of the following: a method further comprising enriching the sample for the fetal cells; a method where the enriching comprises differential expansion of the fetal cells over the maternal cells; a method further comprising analyzing the amplified product identified as containing the fetal allele to detect a fetal genetic variation; a method where the fetal genetic variation is selected from the group consisting of an aneuploidy, a microdeletion, a microduplication, and a mutation or other genetic variation; a method further comprising analyzing the amplified product identified as containing the fetal allele to detect the presence of mosaicism; a method further comprising analyzing the amplified product identified as containing the fetal allele to detect the presence of dizygotic twins; a method where the preamplification comprises whole genome amplification or whole transcriptome amplification; a method where the target loci are homozygous for the maternal genotype; a method where the target loci are heterozygous for the maternal genotype; a method where the target loci comprise a mixture of homozygous and heterozygous loci for the maternal genotype; a method where the amplified product comprises genomic DNA; a method where the amplified product comprises complementary DNA; a method where determining a maternal genotype comprises using a panel of SNPs to genotype a sample of maternal genetic material from the same individual that is the source of the maternal cells; a method where the source of the maternal genetic material is selected from the group consisting of blood, serum, plasma, urine, a cervical swab, or a buccal swab; a method where the source of the maternal genetic material is selected from the group consisting of blood or a buccal swab; a method where the selection of the test locus comprises screening or genotyping a sample of maternal and fetal cell-free nucleic acids for a genotype differing from the maternal genotype at a target locus, and selecting as the test locus a target locus with a non-maternal genotype in the sample of cell-free nucleic acids; a method where the non-maternal genotype is homozygous; a method where the non-maternal genotype is heterozygous; a method where the source of the maternal and fetal cell-free nucleic acid sample is blood, serum, plasma, urine, or a cervical swab from a pregnant woman; a method comprising selecting and screening more than one test locus in a single aliquot; a method comprising selecting and screening more than one test locus in more than one aliquot; a method comprising selecting and screening one test locus in a single aliquot; a method comprising selecting and screening one test locus in more than one aliquot; a method where each subsample comprises not more than one cell; a method further comprising pooling groups of two or more aliquots prior to screening; a method where pooling comprises the use of an indexed system of rows and columns of wells comprising the aliquots; a method where the number of rows and columns are independently between about 2 and about 1000; a method where the number of rows and columns are independently between about 8 and about 100; a method where the number of rows and columns are independently between about 16 and about 24; a method where at least one target locus is homozygous for the maternal genotype; a method where at least one target locus is heterozygous for the maternal genotype; a method where the panel comprises a mixture of homozygous and heterozygous target loci; a method further comprising determining a signal intensity in a subsample comprising the fetal allele, where the signal intensity is analyzed to determine the presence of a genetic variation; a method further comprising determining an overrepresentation or underrepresentation of chromosomal sequences in a subsample comprising the fetal allele compared to a subsample comprising the maternal allele, wherein the overrepresentation or underrepresentation is used to determine the presence of a chromosomal aneuploidy, microdeletion, or microduplication; a method further comprising determining a signal intensity in a subsample comprising the fetal allele, wherein the signal intensity is analyzed to determine the presence of mosaicism; a method further comprising determining a copy number of alleles in a subsample comprising the fetal allele, where the copy number of alleles is analyzed to determine the presence of mosaicism; a method further comprising determining a copy number of alleles in a subsample comprising the fetal allele, where the copy number of alleles is analyzed to determine the presence of a genetic variation; a method where determining a maternal genotype comprises using a panel of SNPs to genotype a sample of maternal genetic material from the same individual that is the source of the maternal cells; a method where the target locus is homozygous and the test locus is heterozygous; a method where the target locus is heterozygous and the test locus is homozygous; a method where the panel comprises a mixture of homozygous and heterozygous target loci; a method where the panel of SNPs is the panel of SNPs as described herein; and a method where the panel is a panel of at least five loci.

Another embodiment of the invention is a method of detecting an informative paternal allele, comprising: obtaining a sample comprising a mixture of maternal and fetal cells; optionally enriching the sample for the fetal cells; dividing the sample or enriched sample into subsamples; optionally dividing the amplified product into aliquots; optionally selecting a set of target loci; determining whether the genetic material of the maternal cells is homozygous or heterozygous at a set of target loci to determine a maternal genotype; optionally selecting a test locus from the set of target loci, where selection optionally comprises screening a sample of mixed maternal and fetal nucleic acids for a genotype differing from the maternal genotype at a target locus, and selecting as the test locus a target locus with a non-maternal genotype in the sample of mixed maternal and fetal nucleic acids; screening or genotyping an aliquot or subsample for the presence of an informative paternal allele, where screening optionally comprises screening the aliquot for a genotype differing from the maternal genotype at least one target or test locus, and where the presence of the genotype differing from the maternal genotype indicates the presence of an informative paternal allele in the aliquot; and identifying the presence of at least one informative paternal allele in at least one aliquot. In some embodiments, the method further comprises: optionally collecting a portion of the aliquot identified as containing the informative paternal allele; and analyzing an aliquot or a collected portion of the amplified product identified as containing the informative paternal allele to detect a genetic variation.

Some embodiments of the invention comprise: a SNP panel where the chromosome-specific panel is directed to a chromosome subject to aneuploidy selected from the group consisting of Chromosomes 13, 18, and 21, X, and Y; and a SNP panel further comprising a control chromosome-specific panel directed to a control chromosome selected from the group consisting of Chromosomes 1, 2, and 3.

The term screening as used in at least one of the priority documents cited above encompasses the methods of screening and genotyping described herein. In addition, the terms homozygous and heterozygous alleles as used in at least one of the priority documents cited above are sometimes referred to herein as heterozygous or homozygous locus or loci, or heterozygous or homozygous genotypes. Further, the term preamplification as used in at least one of the priority documents cited above is referred to herein as subsample amplification.

It will be understood by those of skill in the art that numerous and various modifications can be made without departing from the spirit of the present invention. All the references referred to herein are incorporated by reference in their entirety for the subject matter discussed. The following examples are included for illustrative purposes only and are not intended to limit the scope of the invention.

EXAMPLES

Example 1

The following example of an embodiment of the invention involves PCR-based detection of a fetal sample, followed by WGA. Cells, optionally an enriched mixture of maternal and fetal cells, are suspended in a buffer such as PBS and distributed into a second buffer with appropriate chemistry for cell lysis and PCR. The cells in a PCR compatible buffer are then partitioned into individual reactions, for example by the introduction of oil plugs to create oil separation of individual cells in lysis and PCR buffer. This method preferably uses a chemistry that fulfills a single-step cell lysis, and amplification of target nucleic acids without addition of reagents following encapsulation. This method also preferably does not involve DNA purification prior to DNA amplification. Each nominal single-cell reaction is then subjected to heating and cooling thermal cycling with fetal specific fluorescent probe detection either during the thermal cycling or at the end of the final cycle and detection of all compartments that contain fetal cells (i.e., one or more). In the preferred case, one cell per reaction is obtained, but reactions consisting of one fetal cell and a few to many maternal cells will still correctly identify the presence or absence of a fetal cell. So long as the subsequent genomic analysis tolerates the equivalent contamination (i.e., one fetal cell and two maternal cells implies 33% pure fetal DNA), then more than one cell per reaction is acceptable. Each positive compartment is optionally pooled into a single shared vessel. This pooled, fetal-specific reaction is subjected to DNA clean-up procedures, such as the removal of RNA and proteins. Following the optional cleanup, the nucleic acids are subject to WGA using any compatible chemistry. The methods for WGA include any of the following: Degenerate oligonucleotide primed polymerase chain reaction ("DOP-PCR"), Ligation mediated PCR ("LM-PCR"), Strand Displacement amplification ("SDA") with Φ-29 polymerase, or other combination protocols (Rubicon Genomics, or NuGen). Following WGA, the resulting amplified genomic DNA is used for genetic analysis, for example, comparative genomic hybridization ("CGH") or complete genome sequencing. There are many methods that are used for CGH, including BAC arrays or oligo arrays. There are also a variety of methods for sequencing including standard capillary based Sanger sequencing and current "next-generation" high throughput sequencing platforms, including those offered by Solexa/Illumina (San Diego, Calif.), Complete Genomics (Mountain View, Calif.), Roche/454 (Branford, Conn.), and Life Technologies (SOLiD™) (Carlsbad, Calif.).

Example 2

The following example of an embodiment of the invention for detection of fetal DNA from cells includes isolation of cells into discrete reaction chambers followed by WGA, then separation of each reaction into multiple aliquots for PCR fetal allele detection, and then optionally pooling conjugate aliquots of fetal positive reactions for genetic analysis, e.g., CGH or sequencing. Cells, optionally an enriched mixture of fetal and maternal cells, are distributed into isolated reaction chambers containing appropriate buffers and reagents for cell lysis and WGA. This could be in alternating aqueous and oil phases in capillaries or in a plate format with access to allow multistep reagent addition. In a plate format, cells are first resuspended as about 100,000 cells in 200 μl, and placed into a well of a 96-well plate. Then using standard micropipetting techniques, such as those offered by TECAN (Männedorf, Switzerland), LabCyte (Sunnyvale, Calif.) or others, 10 nL of cell suspension containing an average of 1, 2, 3, 4, or 5 cells are transferred to a high density plate containing, for example, 1,536 or 3,456 wells. Standard WGA chemistries are used. For example, to each 10 nL of cell volume, 90 nL of reagent for WGA is added, the plate is sealed by oil to prevent evaporation, and WGA chemistry is allowed to proceed. Following WGA, up to 25 nL, containing many copies of amplified genomic DNA from all cells in the reaction, is transferred to a second high-density plate. Then an aliquot of up to 100 nL of PCR reagent containing primers and probes to identify fetal DNA containing reactions is screened using a target locus from a SNP panel as disclosed herein. Reactions which are positive for fetal DNA are used, optionally after pooling, for downstream genomic analysis, including CGH or sequencing. The reactions are subjected to clean up procedures prior to CGH hybridization or sequencing.

Example 3

In the following example of an embodiment of the invention, SNPs located on Chromosome 21 are selected for a panel. Hardy-Weinberg equilibrium ("HWE") is assumed to calculate probabilities of allele frequencies. One allele is favored in homozygosity across the major known haplotypes. The maternal genotype is homozygous (pp or qq) at less than 0.25 and the opposite homozygous genotype is at more than 0.25, and the probabilities of the alleles is given by the following equation: $p^2+2pq+q^2=1$. The SNPs are inherited in a Mendelian fashion.

Example 4

In the following example of an embodiment of the invention, a proposed panel involves selecting SNPs at HWE, where the ratios of $p^2$ and $q^2$ are 0.25, and heterozygosity is 0.5. With these ratios, finding homozygous maternal SNPs requires statistically only 20 SNPs to find 10 SNPs where the maternal sample is homozygous (20*(0.25+0.25)). For any given homozygous SNP, the population including the fetus would have a probability of being heterozygous of 0.5. For the first maternal homozygous SNP, the probability of fetal heterozygosity is 0.5, for a total probability of 0.5. For the first and second maternal homozygous SNP, the combined probability is 1−(0.5*0.5)=0.75. The combined probabilities of seven SNPs is 0.992.

Example 5

The following example is an embodiment of the invention. A pregnant female presents at 14 weeks gestational age. To detect whether the fetus has trisomy 21, a physician obtains a 30 mL blood sample and epithelial cells from the pregnant female via venipuncture and buccal swab, respectively.

A panel of SNPs is designed. Twenty SNPs each from Chromosomes 1 and 21 (i.e., 40 target loci) are selected for the panel, with each SNP having a minor allele frequency of 49% across all major populations. Maternal DNA is extracted from the buccal swab and genotyped using the SNP panel. Twenty SNPs from the panel generate a homozygous genotype (i.e., target loci) and are selected for further genotyping in the mixture of maternal and fetal cells from the blood sample.

The blood sample is enriched to 1:10,000 fetal:maternal cells by subjecting the sample to FICOLL™ ([location]), followed by Miltenyi magnetic beads (Gladbach, Germany). The enriched blood sample is suspended in a solution containing lysis buffer and PCR reagents. The sample is then combined with oil plugs and introduced to a microfluidic device such that the sample is divided into subsamples that each comprise not more than one cell. Once inside the microfluidic device, the subsamples undergo a single-step cell lysis, followed by PCR amplification as described below.

A calculation is performed to determine that with a concentration of 1:10,000 fetal:maternal cells, 50,000 cells must be screened to detect about 5 heterozygous loci for a SNP with a minor allele frequency of 49%.

A first set of 50,000 subsamples (and therefore 50,000 cells) is screened subsample-by-subsample (and therefore cell-by-cell) for a first SNP on each of Chromosomes 1 and 21 (i.e., a total of two loci) using multiplex qPCR with the TAQMAN® system. No heterozygous genotypes are identified for either of the SNPs on Chromosome 1 or 21. A second set of 50,000 subsamples is then screened subsample-by-subsample for a second SNP on each of Chromosomes 1 and 21. The SNP on Chromosome 1 is heterozygous (indicating the presence of a fetal allele), while the SNP on Chromosome 21 is homozygous. A third set of 50,000 subsamples is then screened subsample-by-subsample for a third SNP on each of Chromosome 1 and 21. This time, the SNP on Chromosome 21 is heterozygous and no further genotyping is performed.

The ratio of alleles from the third SNP on Chromosome 21 is then analyzed to detect the presence of aneuploidy. Because the allelic intensity of the maternally-derived allele (C) compared to the paternally-derived allele (G) is 2:1 (i.e., CCG), trisomy 21 is detected.

Example 6

The following example is an embodiment of the invention. Fetal and adult cells were grown in the presence of different factors to assess their effect on differential expansion of fetal cells. The factors were Stem Cell Factor at 50 ng/mL, IL-3 at 5 ng/nL, IL-6 at 5 ng/mL, EPO at 1.5 LVmL, TPO at 100 ng/mL, and Flt-3 at 50 ng/mL. The cells were CD34+ positive cells purified from adult mobilized donor peripheral blood and CD34+ positive cells purified from fetal liver tissue purchased from Cambrex (Walkersville, Md.). Cells were plated at 10,000 cells per mL into 24-well tissue culture plates. Cells were incubated in HPGM medium with 50 units/mL of penicillin, 50 μg/mL streptomycin sulfate, and the cytokine combinations above for 6 days at 37° C. and 5% $CO_2$ in a humidified chamber. After six days, an aliquot of cells was counted manually with a hemacytometer and the total cell numbers were calculated using a standard formula. An additional aliquot was used to assay total ATP levels (linear correlation with total cell numbers) using a VIALIGHT® assay kit (Cambrex, Walkersville, Md.).

In every case measured, the fetal cells expanded more than adult cells (e.g., compare the fourth column to the seventh column from Table 4). The final column of Table 4 shows the ratio of fetal cells to adult cells for some grow conditions. In every case where the ratio was measured, fetal cells were more numerous after expansion.

Example 7

The following example of an embodiment of the invention for detection of fetal DNA from cells includes isolation of cells into discrete reaction chambers followed by WGA, and direct detection of genetic variation. Cells, optionally an enriched mixture of fetal and maternal cells, are distributed into isolated reaction chambers containing appropriate buffers and reagents for cell lysis and WGA. In a plate format, cells are first resuspended as about 100,000 cells in 200 μl, and placed into a well of a 96-well plate. Then using standard micropipetting techniques, such as those offered by TECAN (Männedorf, Switzerland), LabCyte (Sunnyvale, Calif.), or others, 10 mL of cell suspension containing an average of 1, 2, 3, 4, or 5 cells are transferred to a high density plate containing, for example, 1,536 or 3,456 wells. Standard WGA chemistries are used. For example, to each 10 nL of cell volume, 90 nL of reagent for WGA is added, the plate is sealed by oil to prevent evaporation, and WGA chemistry is allowed to proceed. Following WGA, PCR reagent containing primers and probes to identify fetal DNA-containing reactions is added to amplify a target locus from a SNP panel as disclosed herein. Reactions which are positive for fetal DNA are directly detected using capture probes in the reaction chambers. Following target hybridization, wells are washed to remove non-target DNA and non-reacted reagents. The specifically hybridized products are then detected using standard chemistries, such as molecular beacons. The ratio of fetal and maternal sequences can then be used to determine genetic variation.

Example 8

The following example is an embodiment of the invention. 40 ml of blood is collected from a pregnant female and combined with a standard anticoagulant (e.g., EDTA), then shipped to a processing location. 12 ml of plasma is removed from the blood and cell-free DNA is extracted. An aliquot of whole blood or PBMCs is removed for maternal genotyping.

Gradient enrichment is performed for red blood cell removal, including red blood cell lysis. Magnetic activated cell sorting (MACS) is used to deplete maternal cells to a yield of less than about 500,000 total cells. Cell sorting is used to enrich the fetal fraction for a total yield of about 10,000 cells. The cells are divided to λ=about 1 cell per reaction in a suitable volume. Cells are lysed directly and a PCR compatible solution is created, possibly with the addition of a neutralization solution. WGA reagents are added to each reaction for a total reaction volume of 100 nl. WGA is allowed to proceed for a total of between about 10 and 10,000 total genomic equivalents of DNA (where a reaction initially contained one genomic equivalent). The WGA reaction is stopped, and all reactions are split into at least one position-indexed aliquot. PCR is performed on all aliquots to detect a non-maternal allele (e.g., by comparing to a genotype obtained using the aliquot of whole blood or PBMCs). The original location of the WGA material containing non-maternal alleles is identified, and the volume at these locations is recovered. These volumes are then pooled for a final WGA to generate a quantity of DNA suitable for aCGH (e.g., about 0.5-1 ug). aCGH is then performed to detect CNVs.

TABLE 2

| Number of SNPs | $p^2$ | 2pq | $q^2$ | Number of Possible Homozygous Maternal SNPs with Cumulative Testing |
|---|---|---|---|---|
| 2 | 0.25 | 0.5 | 0.25 | 1 |
| 4 | 0.25 | 0.5 | 0.25 | 2 |
| 6 | 0.25 | 0.5 | 0.25 | 3 |
| 8 | 0.25 | 0.5 | 0.25 | 4 |
| 10 | 0.25 | 0.5 | 0.25 | 5 |
| 12 | 0.25 | 0.5 | 0.25 | 6 |
| 14 | 0.25 | 0.5 | 0.25 | 7 |
| 16 | 0.25 | 0.5 | 0.25 | 8 |
| 18 | 0.25 | 0.5 | 0.25 | 9 |
| 20 | 0.25 | 0.5 | 0.25 | 10 |

TABLE 3

| | $p^2$ | 2pq | $q^2$ | Cumulative probability of finding at least one heterozygous fetal allele, if the selected maternal SNPs are $p^2$ type |
|---|---|---|---|---|
| SNP1 | 0.25 | 0.5 | 0.25 | 50.00% |
| SNP2 | 0.25 | 0.5 | 0.25 | 75.00% |
| SNP3 | 0.25 | 0.5 | 0.25 | 87.50% |
| SNP4 | 0.25 | 0.5 | 0.25 | 93.75% |
| SNP5 | 0.25 | 0.5 | 0.25 | 96.88% |
| SNP6 | 0.25 | 0.5 | 0.25 | 98.44% |
| SNP7 | 0.25 | 0.5 | 0.25 | 99.22% |
| SNP8 | 0.25 | 0.5 | 0.25 | 99.61% |
| SNP9 | 0.25 | 0.5 | 0.25 | 99.80% |
| SNP10 | 0.25 | 0.5 | 0.25 | 99.90% |
| SNP11 | 0.25 | 0.5 | 0.25 | 99.95% |
| SNP12 | 0.25 | 0.5 | 0.25 | 99.98% |
| SNP13 | 0.25 | 0.5 | 0.25 | 99.99% |
| SNP14 | 0.25 | 0.5 | 0.25 | 99.99% |
| SNP15 | 0.25 | 0.5 | 0.25 | 100.00% |
| SNP16 | 0.25 | 0.5 | 0.25 | 100.00% |
| SNP17 | 0.25 | 0.5 | 0.25 | 100.00% |
| SNP18 | 0.25 | 0.5 | 0.25 | 100.00% |
| SNP19 | 0.25 | 0.5 | 0.25 | 100.00% |
| SNP20 | 0.25 | 0.5 | 0.25 | 100.00% |

TABLE 4

| Cytokine Combination | Total ATP/well (AU) | Fetal cells per well | Fold expansion (fetal) | Total ATP/well (AU) | Adult cells per well | Fold expansion (adult) | Differential ATP Fetal/Adult | Differential count Fetal/Adult |
|---|---|---|---|---|---|---|---|---|
| O | 77.2 | 188500 | 18.85 | 0.8 | 7500 | 0.75 | 93.6 | 25.1 |
| OA | 272.8 | 577500 | 57.75 | 46.2 | 91200 | 9.12 | 5.9 | 6.3 |
| OB | 167.9 | 410400 | 41.04 | 8.9 | 23400 | 2.34 | 18.8 | 17.5 |
| OC | 657.9 | 1410000 | 141 | 100.7 | 127500 | 12.75 | 6.5 | 11.1 |
| OD | 267.0 | 652500 | 65.25 | 18.3 | 37000 | 3.7 | 14.6 | 17.6 |
| OE | 213.5 | 663300 | 66.33 | 70.9 | 150000 | 15 | 3.0 | 4.4 |
| OAB | 280.2 | | | 57.5 | | | 4.9 | |
| OAC | 668.3 | | | 282.6 | | | 2.4 | |
| AOD | 457.9 | | | 95.0 | | | 4.8 | |
| OAE | 517.1 | | | 186.0 | | | 2.8 | |
| OBC | 741.4 | | | 225.8 | | | 3.3 | |
| OBD | 335.9 | 850500 | 85.05 | 38.7 | 123200 | 12.32 | 8.7 | 6.9 |
| QBE | 341.2 | | | 138.6 | | | 2.5 | |
| OCD | 706.0 | | | 260.2 | | | 2.7 | |
| OCE | 638.6 | | | 338.1 | | | 1.9 | |
| ODE | 480.5 | | | 157.6 | | | 3.0 | |
| OABC | 691.0 | | | 323.9 | | | 2.1 | |
| OABD | 389.8 | | | 92.8 | | | 4.2 | |
| OABE | 281.3 | | | 126.5 | | | 2.2 | |
| OACD | 689.6 | | | 326.3 | | | 2.1 | |
| OACE | 609.6 | | | 347.3 | | | 1.8 | |
| OADE | 508.0 | | | 181.6 | | | 2.8 | |
| OBCD | 694.0 | | | 268.7 | | | 2.6 | |
| OBCE | 543.4 | | | 228.4 | | | 2.4 | |
| OBDE | 299.0 | | | 122.2 | | | 2.4 | |
| OCDE | 670.0 | | | 283.4 | | | 2.4 | |
| OABCD | 568.6 | | | 259.4 | | | 2.2 | |
| OABCE | 602.1 | | | 289.0 | | | 2.1 | |
| OABDE | 317.4 | | | 137.4 | | | 2.3 | |
| OACDE | 472.0 | | | 165.0 | | | 2.9 | |
| OBCDE | 441.0 | 1449000 | 144.9 | 215.1 | 292000 | 29.2 | 2.1 | 5.0 |
| OABCDE | 571.3 | 1577000 | 157.7 | 259.8 | 440800 | 44.08 | 2.2 | 3.6 |
| OC | | 1000000 | 100 | | 220000 | 22 | | 4.5 |
| OCD | | 1200000 | 120 | | 350000 | 35 | | 3.4 |
| O | | 450000 | 45 | | 30000 | 3 | | 15.0 |
| OA | | 75000 | 7.5 | | 50000 | 5 | | 1.5 |
| OB | | 550000 | 55 | | 30000 | 3 | | 18.3 |
| OAB | | 625000 | 62.5 | | 100000 | 10 | | 6.3 |
| OE | | 900000 | 90 | | 130000 | 13 | | 6.9 |
| ODE | | 1250000 | 125 | | 160000 | 16 | | 7.8 |

O: Stem Cell Factor (50 ng/mL)
A: IL-3 (5 ng/mL)
B: IL-6 (5 ng/mL)
C: EPO (1.5 U/mL)
D: TPO (100 ng/mL)
E: Flt-3 (50 ng/mL)

What is claimed is:

1. A method of obtaining and analyzing a fetal genome from a mixture of maternal and fetal cells, comprising:
   a) obtaining a maternal blood sample comprising a mixture of maternal and fetal cells;
   b) enriching said sample from step a) for said fetal cells, wherein fetal cells in the mixture of maternal and fetal cells are enriched to between 1 in 100 and 1 in 100,000 fetal cells per maternal cells;
   c) dividing said enriched sample from step b) into at least about 1,000 subsamples, wherein each subsample has an average of less than one cell;
   d) performing whole genome amplification on each at least about 1,000 subsamples from step c) to provide an amplified product for each subsample, wherein each amplified product has an amplified genome from an average of about one cell, and wherein at least 99% of the amplified genomes in said amplified product are not from a fetal cell;
   e) dividing each of said amplified product from step d) into aliquots, wherein each aliquot contains at least one copy of said amplified genome from said cell, and wherein at least 99% of the amplified genomes in said aliquots are not from a fetal cell;
   f) screening or genotyping an aliquot from step e) for the presence of a fetal identifier, wherein said screening or genotyping comprises:
      i) determining a maternal genotype and a fetal genotype at at least 1 SNP(s) per chromosome-specific SNP panel on at least 10 chromosome-specific panels;
      ii) selecting as test loci from step i) at least 1 SNP(s) per chromosome-specific panel on at least 10 chromosome-specific panels where the maternal genotype is homozygous and the fetal genotype is heterozygous;
      iii) screening or genotyping said aliquot from step e) for a genotype differing from a maternal genotype at at least one of said test loci from step ii), wherein the presence of said genotype differing from said maternal genotype indicates the possible presence of an informative paternal allele in said aliquot and thus said corresponding subsample;
      iv) screening or genotyping an aliquot from a subsample having an informative paternal allele from step iii) for a genotype differing from a maternal genotype at at least 1 test loci per chromosome-specific panel on at least 10 chromosome-specific panels from step ii), wherein the presence of said genotype differing from said maternal genotype indicates the presence of an informative paternal allele in said aliquot,
   g) identifying the presence of a fetal cell in at least one subsample from step c) whose aliquot contains an informative paternal allele from step f) iv); and
   h) analyzing another aliquot from step e) from said at least one subsample from step g) identified as containing fetal cell to detect a genetic variation in said genome of said fetal cell.

2. The method of claim 1, wherein said genetic variation is selected from the group consisting of a chromosomal rearrangement, a copy number variation, and a polymorphism.

3. The method of claim 1, wherein said analyzing to detect a genetic variation comprises determining a ratio of maternally- and paternally-inherited alleles, wherein said ratio is analyzed to determine the presence of a genetic variation.

4. The method of claim 1, wherein said analyzing to detect a genetic variation comprises determining a copy number of alleles in said aliquot, wherein said copy number of alleles is analyzed to determine the presence of a genetic variation.

5. The method of claim 1, wherein said maternal genotype and fetal genotype are determined from a mixture of maternal and fetal nucleic acids from a mixture of cell-free nucleic acids.

6. The method of claim 5, wherein the source of said maternal and fetal cell-free nucleic acid sample is blood, serum, plasma, urine, cervical swab, cervical lavage, uterine lavage, or culdocentesis from a pregnant female.

7. The method of claim 1, further comprising pooling an aliquot from two or more subsamples prior to screening or genotyping an aliquot for the presence of a fetal identifier, wherein said screening or genotyping further comprises:
   individually screening or genotyping a second aliquot from the subsamples whose pooled aliquots contained an informative paternal allele.

8. The method of claim 7, wherein said pooling comprises the use of an indexed system of rows and columns of wells comprising said aliquots.

9. The method of claim 1, wherein aliquots from two or more subsamples identified as containing a fetal cell are pooled prior to said analyzing another aliquot from said at least one subsample identified as containing fetal cell to detect a genetic variation in said fetal cell.

10. The method of claim 7, wherein aliquots from two or more subsamples identified as containing a fetal cell are pooled prior to said analyzing another aliquot from said at least one subsample identified as containing fetal cell to detect a genetic variation in said fetal cell.

11. The method of claim 1, wherein the loci used to determine the presence of an informative paternal allele is not the same loci used to detect a genetic variation.

* * * * *